US00PP10947P

United States Patent [19]

Bergman

[11] Patent Number: Plant 10,947

[45] Date of Patent: Jun. 8, 1999

[54] HIBISCUS PLANT NAMED 'CALYPSO WIND'

[75] Inventor: Wendy R. Bergman, Lehigh Acres, Fla.

[73] Assignee: Yoder Brothers, Inc., Barberton, Ohio

[21] Appl. No.: 08/995,357

[22] Filed: Dec. 22, 1997

[51] Int. Cl.[6] ..... A01H 5/00

[52] U.S. Cl. ..... Plt./257

[58] Field of Search ..... Plt./67.8, 257

[56] References Cited

PUBLICATIONS

Usher, The Wordsworth Dictionary of Botany. p. 274, 1966.

*Primary Examiner*—Elizabeth Kemmerer
*Assistant Examiner*—Melissa L. Kimball
*Attorney, Agent, or Firm*—C. A. Whealy

[57] ABSTRACT

A new and distinct cultivar of Hibiscus plant named 'Calypso Wind', characterized by its dark green leaves; upright and outwardly spreading, uniform and symmetrical plant habit that is appropriate for container production; floriferousness with numerous and large dark orange-colored flowers with red to dark red throats; long peduncles; good resistance to flower bud abscission; and excellent postproduction longevity.

1 Drawing Sheet

The present invention relates to a new and distinct cultivar of Hibiscus, botanically known as *Hibiscus rosa-sinensis,* and hereinafter referred to by the cultivar name Calypso Wind.

The new cultivar is a product of a planned breeding program conducted by the inventor in Alva, Fla. The objective of the breeding program is to create new Hibiscus cultivars having uniform and compact plant habits appropriate for container production, early and uniform flowering, numerous flowers per lateral branch, desirable flower color, resistance to flower bud abscission, and good postproduction longevity.

The new cultivar originated from a cross made by the inventor in Alva, Fla., of the *Hibiscus rosa-sinensis* cultivar Tangerine (disclosed in U.S. Plant Pat. No. 8,166) as the female, or seed, parent with the *Hibiscus rosa-sinensis* cultivar Brilliant Red (not patented) as the male, or pollen, parent. The cultivar Calypso Wind was discovered and selected by the inventor as a flowering plant within the progeny of the stated cross in a controlled environment in Alva, Fla., on Sep. 24, 1994.

Compared to plants of the female parent, the Hibiscus cultivar Tangerine, plants of the new Hibiscus have leaves that are not lobed and larger flowers that are darker in flower color. Compared to plants of the male parent, the Hibiscus cultivar Brilliant Red, plants of the new Hibiscus are more uniform in plant habit and more freely branching. In addition, flowers of plants of the new Hibiscus are smaller, but have better substance and are slightly more orange in color compared to flowers of plants of the cultivar Brilliant Red.

Asexual reproduction of the new cultivar by terminal cuttings taken in a controlled environment in Alva, Fla., has shown that the unique features of this new Hibiscus are stable and reproduced true to type in successive generations.

The cultivar Calypso Wind has not been observed under all possible environmental conditions. The phenotype may vary somewhat with variations in environment such as temperature, light intensity, nutrition and water status without, however, any variance in genotype.

The following traits have been repeatedly observed and are determined to be unique characteristics of 'Calypso Wind'. These characteristics in combination distinguish 'Calypso Wind' as a new and distinct cultivar:

1. Dark green leaves.

2. Upright and outwardly spreading, uniform and symmetrical plant habit that is appropriate for container production.
3. Very freely flowering, numerous and large dark orange-colored flowers with red to dark red throats.
4. Long peduncles.
5. Good resistance to flower bud abscission.
6. Excellent postproduction longevity.

BRIEF DESCRIPTION OF THE PHOTOGRAPHS

The accompanying colored photographs illustrate the overall appearance of the new cultivar, showing the colors as true as it is reasonably possible to obtain in colored reproductions of this type.

The photograph at the top of the sheet comprises a side perspective view of typical plant of 'Calypso Wind'.

The photograph at the bottom of the sheet comprises a close-up view of a typical flower of 'Calypso Wind'. Flower and foliage colors in the photographs may appear different from the actual colors due to light reflectance.

DETAILED BOTANICAL DESCRIPTION

The following observations, measurements and values describe plants grown in Alva, Fla., and Keller, Tex., in 28-cm containers during the summer and early autumn with day temperatures ranging from 16 to 35° C. and night temperatures ranging from 10 to 24° C. In the description, color references are made to The Royal Horticultural Society Colour Chart except where general terms of ordinary dictionary significance are used.

Botanical classification: *Hibiscus rosa-sinensis* cultivar Calypso Wind.

Parentage:

*Female or seed parent.*—*Hibiscus rosa-sinensis* cultivar Tangerine, disclosed in U.S. Plant Pat. No. 8,166.

*Male or pollen parent.*—*Hibiscus rosa-sinensis* cultivar Brilliant Red, not patented.

Propagation:

*Type.*—By terminal cuttings.

*Time to initiate roots.*—About 10 days at temperatures of 24° C.

*Time to develop roots.*—About 28 days at temperatures of 24° C.

*Rooting habit.*—Moderately vigorous, thick and well-branched.

Plant description:

*Plant form and growth habit.*—Perennial, evergreen, upright and outwardly spreading, inverted triangle, uniform and symmetrical plant habit. Moderate vigor.

*Branching habit.*—Very freely branching, usually about seven lateral branches develop after removal of terminal apex.

*Plant height, soil level to top of flowers.*—About 38 cm.

*Plant diameter, area of spread.*—About 55 cm.

*Lateral branch description.*—Length: About 27 cm. Diameter: About 9 mm. Texture: Immature, smooth; woody with age.

*Color.*—Immature: Close to 183A with green areas. Mature: Grayish green to brown.

Foliage description:

*Arrangement.*—Alternate, single.

*Length.*—About 9.5 cm.

*Width.*—About 8 cm.

*Shape.*—Cordate/ovate.

*Apex.*—Acute.

*Base.*—Cordate.

*Margin.*—Crenate.

*Texture.*—Glabrous, glossy/shiny on both surface, leathery.

*Color*—Young foliage, upper surface: Brighter and greener than 146A. Young foliage, lower surface: Close to 146A. Mature foliage, upper surface: 147A. Mature foliage, lower surface: Close to 147B.

*Petiole.*—Length: About 4 cm. Diameter: About 4 mm. Texture: Smooth or with very fine pubescence on upper surface. Color: Close to 166A.

Flower description:

*Natural flowering season.*—Usually spring and summer or during periods of warm weather.

*Flower arrangement.*—Flowers arranged singly at terminal leaf axils. Very freely flowering with typically at least five flower buds and/or open flowers per terminal apex. Flowers flat and face upright or outward.

*Flower appearance.*—Large star-shaped single. Intense dark orange-colored petals with red to dark red throat. Flowers are open for about one day before closing. Flowers self-cleaning.

*Flower diameter.*—About 14 cm.

*Flower bud* (*just before showing color*).—Rate of opening: About one day depending on temperatures. Length: About 2.5 cm. Diameter: About 1 cm. Shape: Columnar, oblong.

*Petals.*—Texture: Crepe, satiny. Arrangement: Corolla consists of five petals that overlap. Shape: Spatulate with rounded apex. Margin: Entire, but slightly ruffled. Length: About 7 cm. Width: About 6 cm. Color: Upper surface, when opening: 42A. Lower surface, when opening: 42B. Upper surface, fully opened: 33A; lighter where petals overlap; veins slightly darker than 33A. Lower surface, fully opened: Mostly 33A, pink towards base. Yellowish at right edges of petals. Throat: Red to dark red, 46A/45A/53A.

*Sepals.*—Appearance: Six sepals fused into a star-shaped calyx. Shape: Linear. Texture: Smooth. Color, outer surface: Greener than 144A.

*Peduncles.*—Length: About 6.25 cm, long. Diameter: About 3 mm at apex. Angle: Upright to outward arching with weight of flower. Strength: Strong, flexible. Color: 144A.

*Reproductive organs.*—Androecium: Stamen number: Numerous. Stamen length: About 5 mm. Anther shape: Globular. Anther size: About 1 mm. Amount of pollen: Quite abundant. Pollen color: 21A. Gynoecium: Pistil length: About 7.5 cm. Style color: Apex: 51B. Base: 46A to 47A. Stigma number: Five. Stigma shape: Round. Stigma diameter: About 2.5 mm. Stigma color: 46A. Ovary color: Light green, 154A.

Disease resistance: No known Hibiscus diseases observed to date on plants grown under commercial greenhouse conditions.

Seed production: If cross-pollinated, seed production may be observed. Usually one to twenty seeds per capsule.

It is claimed:

1. A new and distinct Hibiscus plant named 'Calypso Wind', as illustrated and described.

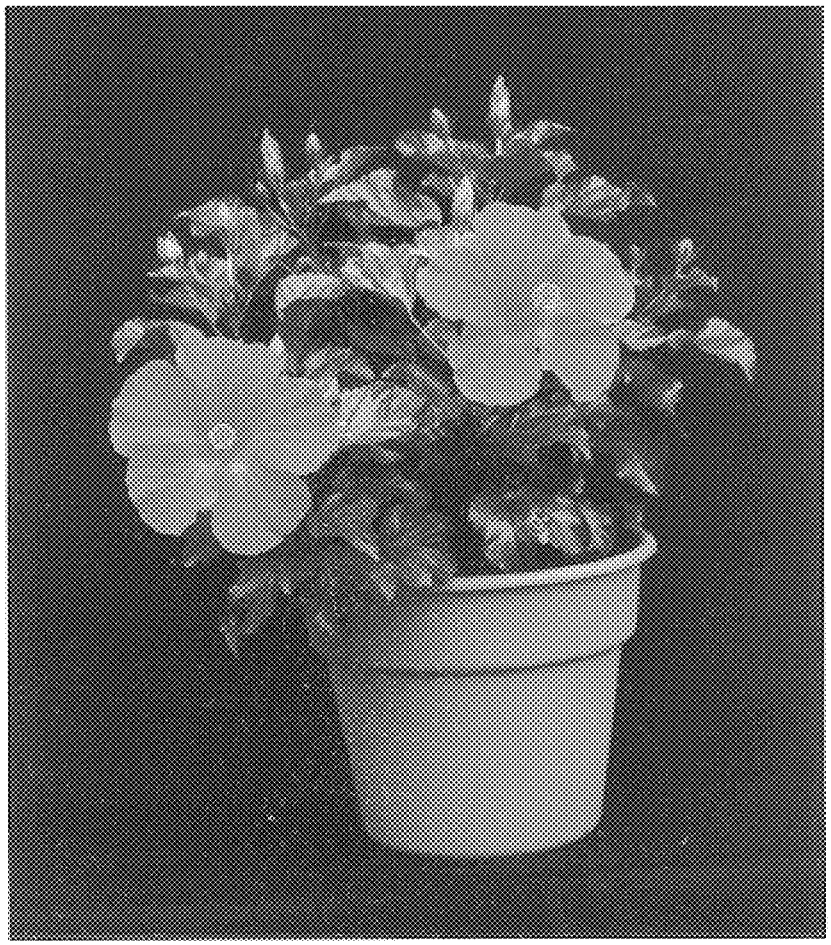
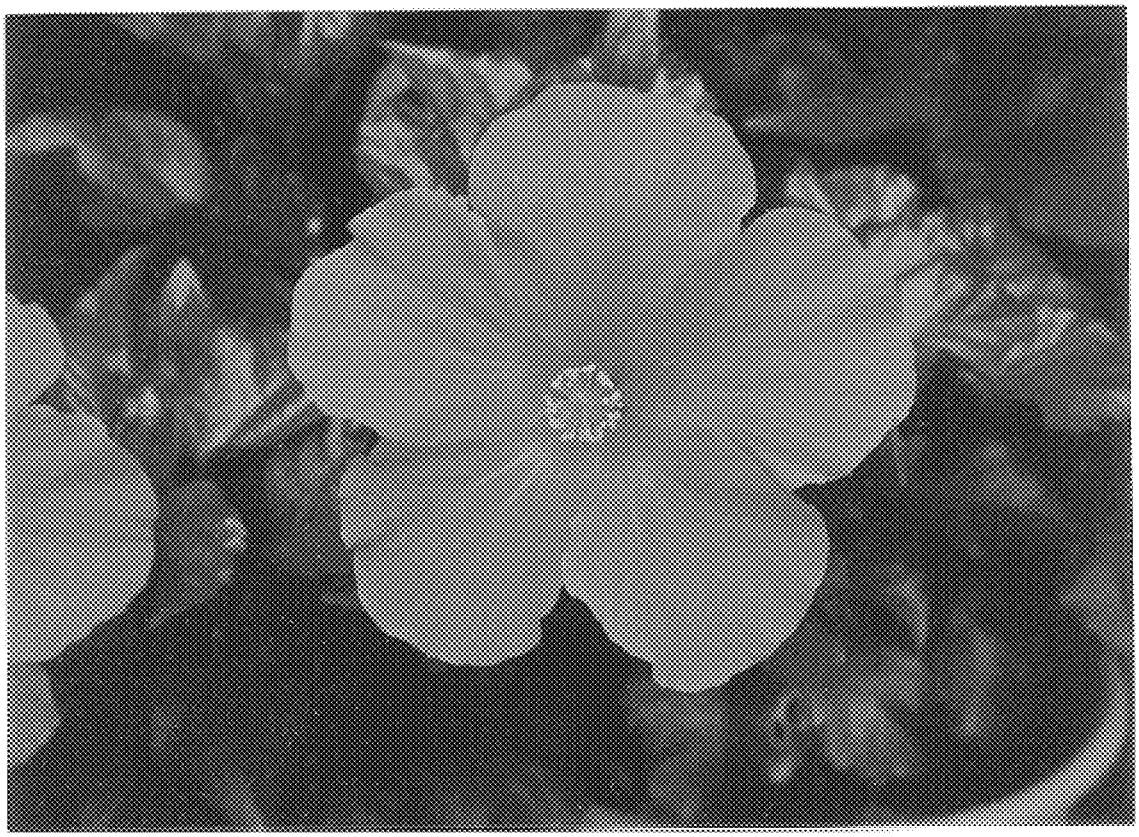

* * * * *